US00RE49691E

(19) United States
(12) Reissued Patent
Ökvist et al.

(10) Patent Number: US RE49,691 E
(45) Date of Reissued Patent: *Oct. 10, 2023

(54) BIOMETRIC USER EQUIPMENT GUI TRIGGER

(71) Applicant: TELEFONAKTIEBOLAGET LM ERICSSON (PUBL), Stockholm (SE)

(72) Inventors: Peter Ökvist, Luleå (SE); Tomas Jönsson, Luleå (SE); David Lindegren, Luleå (SE)

(73) Assignee: Telefonaktiebolaget LM Ericsson (publ), Stockholm (SE)

( * ) Notice: This patent is subject to a terminal disclaimer.

(21) Appl. No.: 17/532,008

(22) Filed: Nov. 22, 2021

Related U.S. Patent Documents

Reissue of:
(64) Patent No.: 9,135,466
Issued: Sep. 15, 2015
Appl. No.: 13/976,295
PCT Filed: Dec. 30, 2010
PCT No.: PCT/IB2010/003488
§ 371 (c)(1),
(2) Date: Jun. 26, 2013
PCT Pub. No.: WO2012/090016
PCT Pub. Date: Jul. 5, 2012

U.S. Applications:
(63) Continuation of application No. 17/086,808, filed on Nov. 2, 2020, now Pat. No. Re. 48,875, which is an (Continued)

(51) Int. Cl.
*G06F 21/62* (2013.01)
*G16H 50/30* (2018.01)

(Continued)

(52) U.S. Cl.
CPC ..... *G06F 21/6218* (2013.01); *A61B 5/00* (2013.01); *G06F 3/011* (2013.01); *G06F 3/0482* (2013.01);

(Continued)

(58) Field of Classification Search
CPC ..... G06F 19/30; G08B 21/02; G08B 21/0202; G08B 21/0446; G08B 21/0453;

(Continued)

(56) References Cited

U.S. PATENT DOCUMENTS 7,170,994 B2 * 1/2007 Kotzin ..... 379/373.01
2003/0038754 A1 * 2/2003 Goldstein et al. ..... 345/7

(Continued)

FOREIGN PATENT DOCUMENTS

EP 2214387 A1 8/2010
GB 2431319 A 4/2007

*Primary Examiner* — Minh Dieu Nguyen

(57) ABSTRACT

A user equipment for providing information most relevant to a user as the user becomes impaired or experiences diminishing capacity is disclosed. The user equipment includes a transceiver, a memory, at least one sensor for detecting a biometric measurement of a user of the equipment, a user interface and a processor. The processor filters the biometric measurement, calculates a metric based on the measurement, evaluates the metric, selectively adjusts an amount of information displayed on the user interface based on the evaluated metric and executes an application corresponding to a user actuation of an item of the displayed information.

56 Claims, 7 Drawing Sheets

Related U.S. Application Data application for the reissue of Pat. No. 9,135,466, and a continuation of application No. 16/291,981, filed on Mar. 4, 2019, now Pat. No. Re. 48,339, which is an application for the reissue of Pat. No. 9,135,466, and a continuation of application No. 15/703,212, filed on Sep. 13, 2017, now Pat. No. Re. 47,372, which is an application for the reissue of Pat. No. 9,135,466.

(51) Int. Cl.

| | |
|---|---|
| ***G16H 40/63*** | (2018.01) |
| ***G16Z 99/00*** | (2019.01) |
| ***H04M 1/72475*** | (2021.01) |
| ***H04M 1/724*** | (2021.01) |
| ***H04M 1/72454*** | (2021.01) |
| ***H04M 1/72418*** | (2021.01) |
| ***A61B 5/00*** | (2006.01) |
| ***G06F 3/01*** | (2006.01) |
| ***G06F 3/0482*** | (2013.01) |

(52) U.S. Cl.
CPC ..... *G16H 40/63* (2018.01); *G16H 50/30* (2018.01); *G16Z 99/00* (2019.02); *H04M 1/724* (2021.01); *H04M 1/72418* (2021.01); *H04M 1/72454* (2021.01); *H04M 1/72475* (2021.01); *H04M 2250/10* (2013.01); *H04M 2250/12* (2013.01)

(58) Field of Classification Search
CPC ..... G16H 10/20; G16H 10/40; G16H 10/60; G16H 10/65; G16H 15/00; G16H 20/00; G16H 20/10; G16H 20/13; G16H 20/17; G16H 20/30
See application file for complete search history.

(56) References Cited

U.S. PATENT DOCUMENTS

| | | | |
|---|---|---|---|
| 2009/0085873 | A1 | 4/2009 | Betts et al. |
| 2009/0267774 | A1 | 10/2009 | Enegren et al. |
| 2014/0114680 | A1 | 4/2014 | Mills et al. |

* cited by examiner

BIOMETRIC USER EQUIPMENT GUI TRIGGER

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. patent application Ser. No. 13/976,295, filed Jun. 26, 2013, now U.S. Pat. No. 9,135,466 B2, granted Sep. 15, 2015, which was a National Stage Entry of International Patent Application No. PCT/IB10/03488, filed Dec. 30, 2010. The reissue applications are (1) U.S. application Ser. No. 15/703,212; (2) U.S. application Ser. No. 16/291,981; (3) U.S. application Ser. No. 17/086,808; and (4) the present application:*

*(1) U.S. application Ser. No. 15/703,212 was filed on Sep. 13, 2017 as an application for reissue of U.S. Pat. No. 9,135,466 B2. It issued as RE47,372 on Apr. 30, 2019.*

*(2) U.S. application Ser. No. 16/291,981 was filed on Mar. 4, 2019 as a continuation reissue application for reissue U.S. application Ser. No. 15/703,212. It issued as RE48,339 on Nov. 11, 2020.*

*(3) U.S. application Ser. No. 17/086,808 was filed on Nov. 2, 2020 as a continuation reissue application for reissue U.S. application Ser. No. 16/291,981. A Notice of Allowance for U.S. application Ser. No. 17/086,808 was mailed on Oct. 18, 2021.*

*(4) The present application is a continuation reissue application for reissue U.S. application Ser. No. 17/086,808, for which a Notice of Allowance was mailed on Oct. 18, 2021.*

*The disclosures of all of these documents are fully incorporated herein by reference.*

TECHNICAL FIELD

The present invention relates to mobile devices and more particularly to methods for adjusting the mobile device user interface to assist a user based on user biometric measurement(s).

BACKGROUND

The use of sensors for assisting users that are impaired in some manner is known. Sensor networks in cars such as that described in U.S. Patent Publication No. 2009/0267774 ("Automobile Physiological Monitoring System and Method for Using the same") prohibit operation of the car by a user experiencing low blood sugar levels in order to prevent accidents/damages.

Phones have been designed for people with certain handicaps or bad eyesight. These phones include big buttons and are often not equipped with many features that demand a high resolution display or more fine grained controllers.

These phones lack features that are common in other phones such as location sensing (GPS for example), music playing and web browsing. They also require entering the numbers (i.e. dialing using fingers) to make a call and a relatively rudimentary phone book.

Other special phones, such as that described in GB 2431 319 ("Phone for Vulnerable Persons") for example, are also static and cannot be used as a normal phone or smartphone. They are not designed to assist the user in making the choice that is appropriate for the user's current health condition or to take into account a sudden change in his or her condition.

Smartphones typically include a graphical user interface (GUI) for providing a logical and intuitive interface for making calls, texting or browsing the web for example. An increasing amount of information is being displayed on the smartphone interface as the size, functionality and quality of the user interface continues to increase. Icons, color, shape and animation can be used to convey or highlight information on the mobile device.

While increasing functionality is attractive to users, excessive information displayed on the user interface impedes a user from effectively utilizing the device especially when the user is operating in a diminished capacity such as due to illness or the like.

Normal phones and "easy to use" smartphones still require several steps for a user to take in order to make a call even from the phones contact list. This could be a problem when a person is not even coherent enough to know the emergency number such as "112" in some countries or "911" in the United States or not able to see well enough to distinguish between digits or remember what the required call sequence looks like. Typically, a high density of information on the smartphone user interface ("cluttering") makes the telephone confusing to use when a user is impaired. Small icons could be misinterpreted and pressing a button to start a game for example might make the situation even worse.

There exists a need for a mobile device which facilitates easier operation for a user experiencing diminishing or diminished capacity.

SUMMARY

It should be emphasized that the terms "comprises" and "comprising", when used in this specification, are taken to specify the presence of stated features, integers, steps or components; but the use of these terms does not preclude the presence or addition of one or more other features, integers, steps, components or groups thereof.

A user equipment provides information on the user interface that is relevant to assisting a user of the equipment when the user equipment detects a diminished capacity or impairment of the user.

According to an exemplary embodiment, a user equipment is disclosed. The user equipment includes a transceiver, a memory, at least one sensor for detecting a biometric measurement of a user of the equipment, a user interface and a processor. The processor filters the biometric measurement, calculates a metric based on the measurement, evaluates the metric, selectively adjusts an amount of information displayed on the user interface based on the evaluated metric and executes an application corresponding to a user actuation of an item of the displayed information.

In other embodiments, a communication method is disclosed. The method includes obtaining at least one biometric measurement of a mobile device user, filtering the at least one obtained measurement, calculating a metric based on the filtered measurement, evaluating the metric, selectively adjusting an amount of information displayed on the mobile device based on the evaluated metric and actuating an item of information displayed on the user equipment.

In further exemplary embodiments, a computer program comprising computer readable program modules is disclosed. The computer program, when run on a user equipment, causes the user equipment to obtain at least one biometric measurement of a mobile device user, filter the at least one obtained measurement, calculate a metric based on the filtered measurement, evaluate the metric, selectively adjust an amount of information displayed on the user equipment based on the evaluated metric and actuate an item of information displayed on the user equipment.

BRIEF DESCRIPTION OF THE DRAWINGS

The objects and advantages of the invention will be understood by reading the following detailed description in conjunction with the drawings in which.

DETAILED DESCRIPTION

Figure 1:
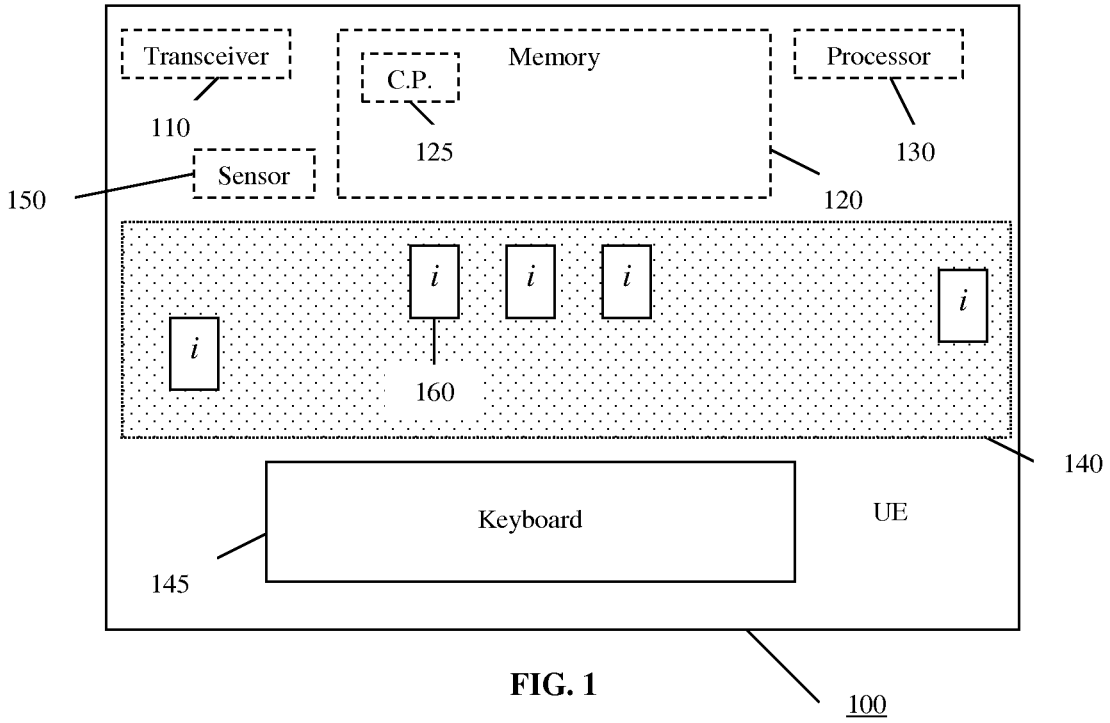
FIG. 1 illustrates a user equipment according to exemplary embodiments.

The various features of the invention will now be described with reference to the figures, in which like parts are identified with the same reference characters.

The various aspects of the invention will now be described in greater detail in connection with a number of exemplary embodiments. To facilitate an understanding of the invention, many aspects of the invention are described in terms of sequences of actions to be performed by elements of a computer system or other hardware capable of executing programmed instructions. It will be recognized that in each of the embodiments, the various actions could be performed by specialized circuits (e.g., analog and/or discrete logic gates interconnected to perform a specialized function), by one or more processors programmed with a suitable set of instructions, or by a combination of both. The term "circuitry configured to" perform one or more described actions is used herein to refer to any such embodiment (i.e., one or more specialized circuits and/or one or more programmed processors). Moreover, the invention can additionally be considered to be embodied entirely within any form of computer readable carrier, such as solid-state memory, magnetic disk, or optical disk containing an appropriate set of computer instructions that would cause a processor to carry out the techniques described herein. Thus, the various aspects of the invention may be embodied in many different forms, and all such forms are contemplated to be within the scope of the invention. For each of the various aspects of the invention, any such form of embodiments as described above may be referred to herein as "logic configured to" perform a described action, or alternatively as "logic that" performs a described action.

According to exemplary embodiments, biometric measurements of a user may be utilized to minimize or reduce (or adjust) the amount of information that is displayed on a user interface of a mobile device which may also be referred to as a mobile communication device or a user equipment (UE) such as a smartphone. The biometric measurements may be obtained by a plurality of sensors. The sensors may obtain a variety of user biometric measurements including, but not limited to, heart rate, blood pressure, perspiration, etc.

The sensors may be integrated within the mobile device or may transmit the biometric measurements to the mobile device. In some embodiments, the sensors may be within a short communication range of the mobile device.

As a user experiences symptoms associated with a deteriorating health or physical condition, the amount of information (or choices available to the user) displayed on the user equipment display is reduced to only display information that is more pertinent to the user in his or her current condition as determined by the biometric measurements. This information may assist the user in communicating his or her condition or seek appropriate help or assistance. Such reduction simplifies the process needed to assist the user such as in finding and using emergency phone numbers, directions to the nearest emergency room/doctor or a pharmacy and the like.

Many mobile devices such as smartphones include sensors for measuring acceleration (e.g. accelerometers) and detecting location (GPS) for example.

Future mobile devices can easily be equipped with other sensors to obtain various biometric measurements of the user. These measurements can be evaluated individually or combined to determine a present condition of the user.

A mobile device may include biometric sensors for detecting or measuring, for example, blood pressure (BP), pulse (P), hand humidity (HH), hand/body shakiness (HS), blood oxygen levels (O2), etc.

The GUI of the phone may change according to the measured biometric condition of the user. That is, the type of information displayed on the interface may change according to the biometric measurement(s) of the user in some embodiments. The functionality that is made available to the user via icons on the interface may also be reduced to reflect the user's current condition. The assumption is that the biometric measurements reflect a deterioration in the user's physical and/or mental condition.

A smartphone (or user equipment) 100 is illustrated in FIG. 1. Smartphone 100 may include, inter alia, a transceiver 110, a memory 120, a processor 130, a user interface 140 such as a graphical user interface (GUI), a keyboard or an on-screen virtual keyboard 145 and a plurality of icons 160 as known in the art. The icons may launch a particular application such as a browser for accessing the internet or for accessing a particular website on the internet or for communicating with a particular destination for example. The icons may also be tagged with the identity (and phone number) for a particular entity such as home, spouse, work, emergency, hospital, doctor, etc. A smartphone according to exemplary embodiments may also include at least one biometric sensor 150. Certain aspects of user equipment 100 (such as memory 120, sensor 150, etc.) are represented by dashed lines to indicate that they may be internal to the user equipment.

Figure 2:
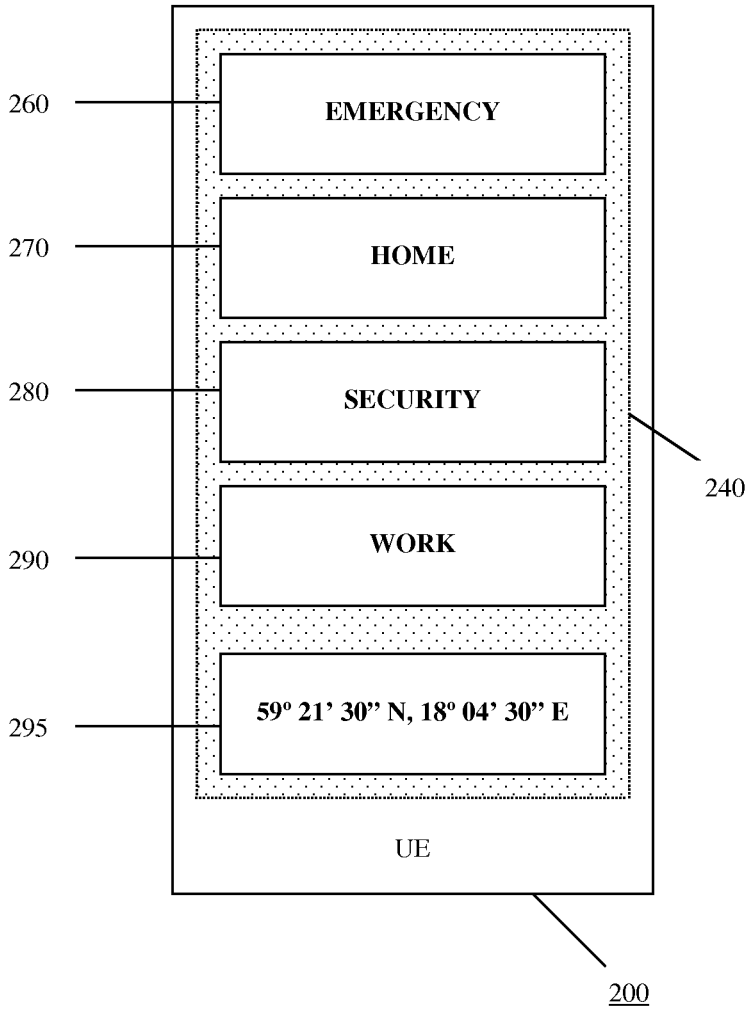
FIGS. 2, 3 and 4 illustrate a user equipment displaying various amounts of information on the user interface according to exemplary embodiments.

As illustrated in FIG. 2, the information displayed on the interface 240 of user equipment 200 may reflect the user's lowered capabilities (based on the biometric measurements) if certain triggers and thresholds for the user's conditions are reached. The change in the amount of information may be gradual if the user's condition worsens slightly. If a user's heart or pulse rate increases suddenly but other sensors do not detect additional changes, a simplified GUI might display icons for dialling for an emergency 260, home 270, security 280 and work 290 as well as user location co-ordinates 295 for example. This list is illustrative and not an exhaustive list of actual conditions.

Figure 3:
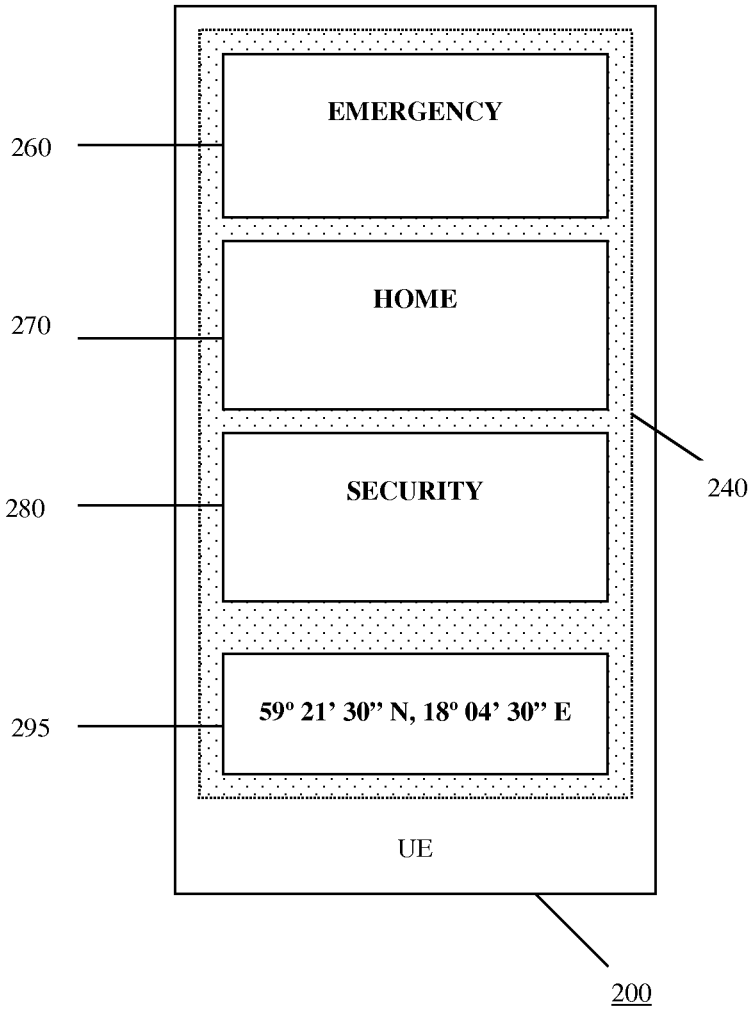
Figure 4:
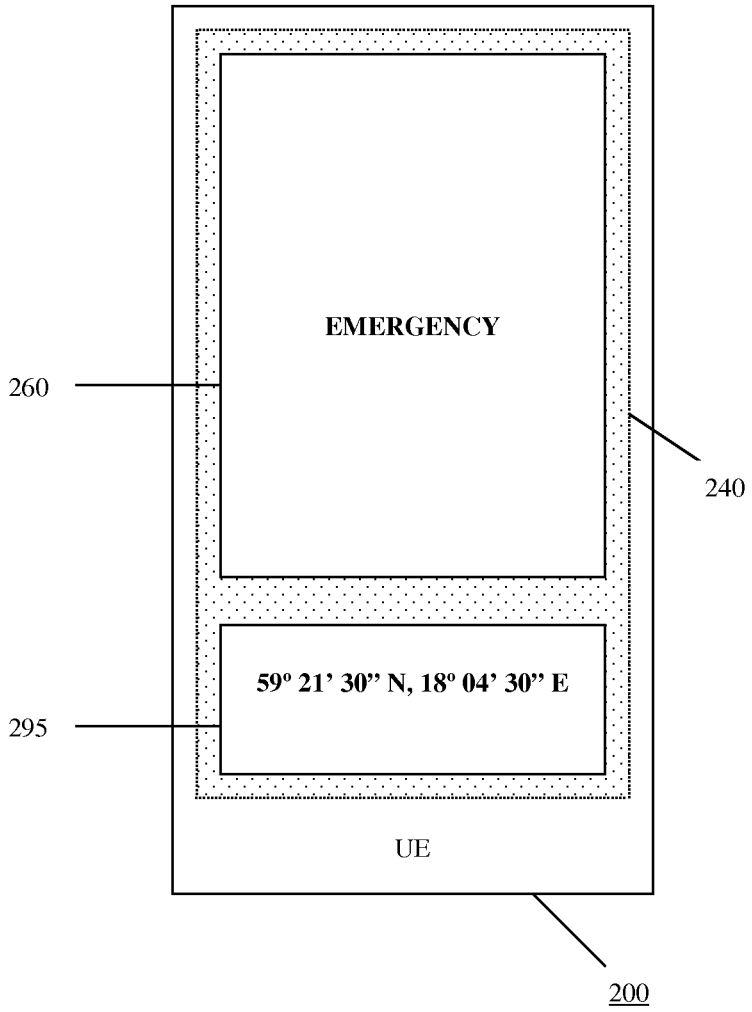

If the heart/pulse rate increases along with an increase in other conditions such as blood pressure, the icons for work may be removed and only the icons for emergency 260, home 270 and security 280 along with location co-ordinates 295 may be displayed on user interface 240 as illustrated in FIG. 3. If the detected conditions indicate further deterioration, the user interface 240 may display only the icon for emergency 260 as illustrated in FIG. 4.

The size of the icons representing each of the contacting entities may also be adjusted based on the number of icons displayed which may also reflect the condition of the user. That is, in an extreme emergency, a relatively large icon for emergency may occupy virtually the entire user interface.

A change in the information displayed on the interface may be drastic (i.e. a sudden change in the type and amount of information displayed) if a sudden deterioration in the user's condition is detected by the sensor(s). A scaled distress level may also be assigned to the user's condition. The determination of a user's capacity may be based on one of the enumerated conditions in some embodiments; in other embodiments, the determination may be made by combining a number of these conditions to determine the user's capacity. An algorithm may be developed or existing algorithms may be implemented for evaluating the user's condition based on biometric measurements from one or more (biometric) sensors.

Figure 5:
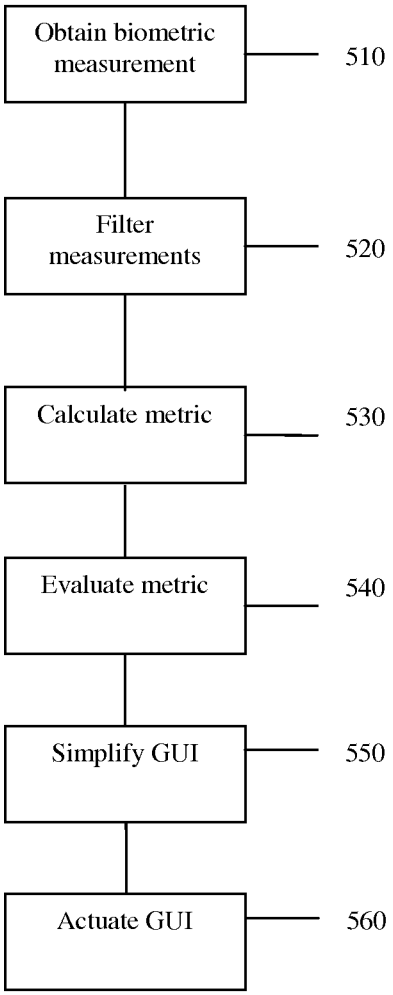
FIGS. 5, 6 and 7 illustrate methods in accordance with exemplary embodiments.

FIG. 5 illustrates a flow/process for triggering a simplified GUI according to exemplary embodiments. The decision calculations may be triggered by significant or very apparent differences in a plurality of biometric measurements in order to preserve battery and processing power. The biometric sensors could be included in the mobile device in some embodiments. Some biometric sensors may be external to the mobile device such as heart rate monitors from a pacemaker and accelerometers such as those inside a collision detector of a car for example.

In the exemplary embodiment of FIG. 5, biometric measurements relating to blood pressure (BP), pulse (P), hand humidity (HH) and hand shakiness (HS) may be used as input values. Hand shakiness may result if an accelerometer of the mobile device detects a particular type of movement (i.e. with a particular magnitude and frequency) that may be indicative of shakiness of a hand.

While these measurements (i.e. BP, P, HH and HS) have been mentioned herein as examples, the number of measurements parameters may be greater or less than this number (i.e. four) in various embodiments. Similarly, the types of measurement may also differ in various embodiments. Other biometric measurements may include temperature, blood sugar levels, etc.

These measurements may be obtained by the mobile device at 510. In this context, "obtain" may imply that the mobile device has access to the measurements as they could be made by sensors that are both part of the mobile device and by sensors that are not part of the mobile device. They may also be in a memory associated with the mobile device.

The measurement may be filtered at 520. Filtering may include accepting measurements that meet a threshold value for example. Filtering may also include removing unwanted bias in the measurements or removing measurements that change too quickly. A state metric (SM) may be calculated at 530 based on the obtained biometric measurement. The SM may be a combination of various biometric measurements—this may be similar to a health care provider considering multiple symptoms simultaneously to determine a user condition.

The state metric calculation is described in further detail below with reference to FIG. 6. The state metric may then be evaluated at 540. The evaluation may include comparing the state metric with a threshold or interpretation triggers and described in further detail below with reference to FIG. 7.

Based on the metric evaluation, a simplified (i.e. less "cluttered") graphical user interface (GUI) with reduced number of icons may be displayed to the user for actuation at 550. One of the items (or icons) displayed on the user interface may be selected or actuated at 560 to establish a do communication link. Actuation may include selecting an icon displayed on the user interface for example. In some situations (such as an extreme emergency), only one item may be displayed for selection/actuation. Upon establishing the connection, the user may communicate his/her condition or seek help or assistance.

Figure 6:
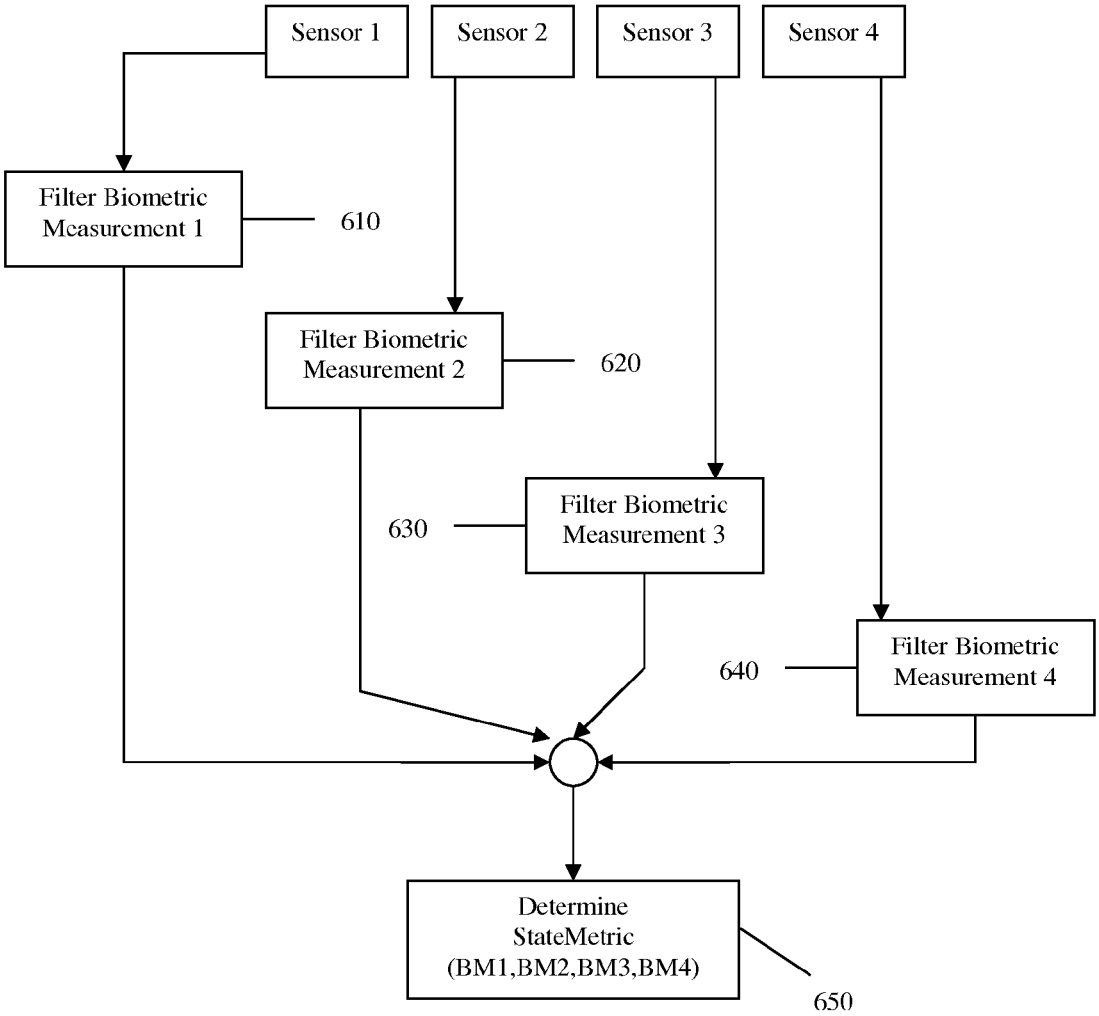

An exemplary flow/process for filtering (corresponding to step 520 of FIG. 5) and transforming the obtained measurements as inputs to calculating the state metric is illustrated in FIG. 6. In each of steps 610, 620, 630 and 640, one of the four exemplary biometric measurements may be filtered. That is, the blood pressure measurement may be filtered at 610; the pulse measurement may be filtered at 620, etc. The filtering may, in some embodiments, include removing noise or bias (such as the user's normal state for example) from the biometric measurements. The filtering may also include examining whether the measurement is steady or irregular (for heart rate for example). An auto correlation function may be utilized to determine if the peaks are where they should be for example.

The state metric may be determined at step 650 based on the filtered values. The state metric may then be provided as input to a state metric evaluation process, which is described in further detail below with reference to FIG. 7.

Figure 7:
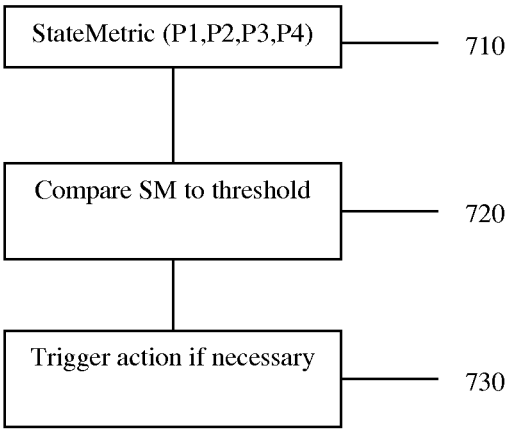

An exemplary state metric evaluation process is illustrated in FIG. 7. The state metric (SM) may be received at 710. SM may be evaluated at 720. Evaluation may comprise comparing the SM to a pre-specified (or pre-determined) threshold value. If the comparison indicates that the user of the mobile device is in a deteriorated or impaired condition, the amount of information on the user interface may be reduced at 730 (i.e. reduced number of icons, displaying icons relevant to the user's condition, etc.).

Multiple biometric measurements may also be evaluated individually in some embodiments In some situations, a particular (single) biometric measurement may trigger an indication that the user's condition requires the display to reduce the amount of information displayed and made available to the user for actuation. However, the amount of displayed information or icons may be reduced further if other parameters also exceed a safe threshold level or if a combination of parameters exceed a threshold. That is, if multiple thresholds (both individual and combined) are exceeded, the amount of information being made available to the user may continue to be decreased based on the particular situation.

A plurality of different counters may be increased or decreased depending on the values of the various biometric measurements (e.g. BP, P, HH, HS). As described, these can be individual measurements or combined measurements depending on the particular metrics available from the mobile device. These metrics can also be given different weights and priorities to produce an accurate response from the mobile device. Based on the metric evaluation, a level of inability or impairment for the user may be determined. In some embodiments, a type of impairment (such as a diagnosis of a condition or disease for example) may also be determined based on the metric evaluation. The amount and type of information displayed on the user interface may be based on the level and/or type of inability determined for the user by evaluation of the metric.

The results of the evaluation can be implemented in several ways depending on the metrics that are available. One strategy could be used if there is only one response. More advanced variants could be used if there are several levels of distress that should be considered by the mobile device.

For example, in the figure with several choices of phone numbers (FIG. 1), the four numbers could be chosen differently depending of the type distress. If it is a car-crash or similar it could give only one response but if it is a case of too low blood sugar, high blood pressure, etc. it could present the number to the personal doctor, etc.

The particular algorithm(s) used for evaluating the various biometric measurements can vary depending on the intended users, or regions of usage, for the mobile device. The algorithms may be known and are not described further herein.

In some embodiments, calculated and evaluated metric(s) may be stored. The storage may have a particular application in cases where the user may have passed out or became unconscious by the time emergency help arrives. In such cases, the emergency personnel can access the user condition information from the mobile device.

In one embodiment, in order for the processor 130 of FIG. 1 to be able to perform the steps illustrated in FIG. 5, the memory comprises a computer program (CP) 135 with computer program modules which when run by the processor 130 causes the mobile communication device to perform all or some of the steps illustrated in FIG. 5. The memory may for example be a flash memory, a RAM (Random-access memory) ROM (Read-Only Memory) or an EEPROM (Electrically Erasable Programmable ROM), and the computer program modules described above could in alternative embodiments be distributed on additional memories (not shown) in the user equipment 100. The processor may not only be a single CPU (Central processing unit), but could comprise two or more processing units in user equipment 100. For example, the processor may include general purpose microprocessors, instruction set processors and/or related chips sets and/or special purpose microprocessors such as ASICs (Application Specific Integrated Circuit). The processor may also comprise board memory for caching purposes.

While the description above focuses on a degradation or worsening of a user condition, exemplary embodiments may also increase the amount of displayed information if an improvement in the user's condition is detected.

While the user is presented with a reduced number of icons and functionality as described above, all the capabilities of a mobile device continue to remain available even if some of the icons are not displayed on the user interface. An icon or a particular gesture or pattern may be actuated on the user interface to retrieve the default display if the user is able to actuate the small icon.

Exemplary embodiments as described herein are not limited to assisting users suffering from physical impairment or diminished capacity. A user may be listening to music while engaged in a physical activity such as running. Biometric sensors may determine that the user is running based on elevated heart rate, shaking or vibration associated with running, etc. The features available to the user may be simplified or reduced to "play", "skip", "pause", "stop", etc.

Various embodiments consistent with the invention provide one or more advantages over conventional systems.

A user will be able to make emergency or important calls even when severely stressed or ill without having to have a specific device for emergency use. Exemplary embodiments can be implemented on a normal Smartphone without having to remove or replace existing features in order to provide the features as described above. There is no need for additional (special) buttons that may limit the user interface in other ways.

Exemplary embodiments as described above predicts the user's capacity/ability and present information that is most suitable or appropriate to the user's condition. In a more severe distress situation, a mobile device according to exemplary embodiments can present the information in less over-crowded manner thus makes it easier for a user to comprehend and use. Furthermore, exemplary embodiments may be implemented on any touch screen device.

The invention has been described with reference to particular embodiments. However, it will be readily apparent to those skilled in the art that it is possible to embody the invention in specific forms other than those of the embodiment described above. The described embodiments are merely illustrative and should not be considered restrictive in any way. The scope of the invention is given by the appended claims, rather than the preceding description, and all variations and equivalents which fall within the range of the claims are intended to be embraced therein.

The invention claimed is:

[1. A user equipment comprising:
- a transceiver;
- a memory;
- at least one sensor for detecting biometric measurements of a user of the equipment;
- a user interface; and
- a processor configured for:
  - filtering the biometric measurements;
  - calculating a metric based on the filtered biometric measurements;
  - evaluating the metric;
  - selectively adjusting an amount of information displayed on the user interface based on the evaluated metric; and
  - executing an application corresponding to a user actuation of an item of the displayed information.]

[2. The user equipment of claim 1, wherein the biometric measurement includes measurements for at least one of blood pressure, pulse, humidity and hand shakiness of the user.]

[3. The user equipment of claim 1, wherein the processor is further configured for evaluating the metric by comparing the metric to a threshold value.]

[4. The user equipment of claim 1, wherein the processor is further configured for reducing the amount of information displayed if the evaluated metric indicates a worsening user condition.]

[5. The user equipment of claim 1, wherein the processor is further configured for:
- increasing the amount of information displayed if the evaluated metric indicates an improvement in the user condition.]

[6. The user equipment of claim 1, wherein the processor is further configured for:
- determining a type of information that is displayed on the user interface.]

[7. The user equipment of claim 1, wherein the processor is further configured for:
- storing the at least one biometric measurement and the evaluated metric.]

[8. A communication method, comprising:

obtaining at least one biometric measurement of a mobile device user;

filtering the at least one obtained measurement;

calculating a metric based on the filtered measurement;

evaluating the metric;

selectively adjusting an amount of information displayed on the user equipment based on the evaluated metric; and actuating an item of information displayed on the user equipment.]

[9. The method of claim 8, wherein the biometric measurement includes at least one of blood pressure, pulse, hand humidity and shakiness of a hand of the user.]

[10. The method of claim 9, wherein the biometric condition is measured by at least one sensor.]

[11. The method of claim 10, wherein the sensor is integral to the mobile device.]

[12. The method of claim 10, wherein the sensor is separate from the mobile device.]

[13. The method of claim 12, wherein the sensor communicates with the mobile device over a short range communication interface.]

[14. The method of claim 8, further comprising reducing the amount of information displayed on the user interface if the metric evaluation indicates an impairment of the user.]

[15. The method of claim 8, further comprising:

determining a type of information that is displayed based on the evaluated metric.]

[16. The method of claim 8, wherein the displayed information includes at least one icon.]

[17. The method of claim 8, wherein the displayed information includes phone numbers of emergency contacts for the user.]

[18. The method of claim 8, further comprising:

increasing the amount of information displayed on the user interface if the metric evaluation indicates an improved condition of the user.]

[19. The method of claim 8, further comprising:

storing the biometric measurements and the evaluated metric for subsequent retrieval and diagnosis.]

[20. A non-transitory computer-readable medium storing a computer program comprising computer readable program modules which when run on a user equipment causes the user equipment to:

obtain at least one biometric measurement of a mobile device user;

filter the at least one obtained measurement;

calculate a metric based on the filtered measurement;

evaluate the metric;

selectively adjust an amount of information displayed on the user equipment based on the evaluated metric; and actuate an item of information displayed on the user equipment.]

[21. The user equipment of claim 1, wherein the calculated metric is a combination of a plurality of biometric measurements.]

*22. A mobile device comprising:*

*a transceiver;*

*a memory;*

*and*

*processing circuitry configured to:*

*display a plurality of icons on a graphical user interface of the mobile device;*

*obtain, from a sensor for measuring acceleration, a measurement of acceleration of a user of the mobile device;*

*obtain, from at least one additional sensor, at least one biometric measurement of the user of the mobile device;*

*reduce a number of the icons displayed on the graphical user interface based on the measurement of acceleration and the at least one biometric measurement; and*

*establish a communication link corresponding to a user selection of a displayed icon.*

*23. The mobile device of claim 22, wherein the reduced number of icons displayed comprises only a single icon.*

*24. The mobile device of claim 23, wherein the single icon comprises an icon for dialing an emergency number.*

*25. The mobile device of claim 24, wherein the icon for dialing an emergency number occupies virtually the entire graphical user interface.*

*26. The mobile device of claim 22, wherein the processing circuitry is further configured to adjust sizes of the reduced number of icons based on the number of icons displayed.*

*27. The mobile device of claim 22, wherein the at least one biometric measurement includes measurements for at least one of heart rate, blood pressure, pulse, hand humidity, perspiration, blood oxygen level, temperature, blood sugar level, and hand shakiness of the user.*

*28. The mobile device of claim 22, wherein the number of icons displayed on the graphical user interface are reduced by calculating a metric based on at least one of the acceleration measurement and the at least one biometric measurement and comparing the metric to a threshold value.*

*29. The mobile device of claim 28, wherein the calculated metric is a combination of a plurality of measurements obtained from one more of the sensor for measuring acceleration and the at least one additional sensor.*

*30. The mobile device of claim 22, wherein one or more of the sensor for measuring acceleration and the at least one additional sensor is integrated into the mobile device.*

*31. The mobile device of claim 22, wherein one or more of the sensor for measuring acceleration and the at least one sensor is separate from the mobile device.*

*32. The mobile device of claim 31, wherein one or more of the sensor for measuring acceleration and the at least one additional sensor communicates with the mobile device over a short range communication interface.*

*33. The mobile device of claim 22, wherein the reduced number of icons displayed comprises icons that are more pertinent to the user in his or her current condition, as determined by the measurement of acceleration and the at least one biometric measurement.*

*34. The mobile device of claim 22, wherein the reduced number of icons displayed comprises an icon for dialing an emergency number.*

*35. The mobile device of claim 22, wherein establishing the communication link comprises one of the following:*

*launching an internet browser;*

*making a phone call;*

*launching a navigation application; or*

*sending a text message.*

*36. The mobile device of claim 22, wherein the sensor for measuring acceleration is an accelerometer.*

*37. The mobile device of claim 22, wherein one or more of the measurement of acceleration and the at least one biometric measurement indicate a worsening user condition.*

*38. A communication method performed by a mobile device, the method comprising:*

*displaying a plurality of icons on a graphical user interface of the mobile device;*

*obtaining, from a sensor for measuring acceleration, a measurement of acceleration of a user of the mobile device;*

*obtaining, from at least one additional sensor, at least one biometric measurement of the user of the mobile device;*

*reducing a number of the icons displayed on the graphical user interface based on the measurement of acceleration and the at least one additional biometric measurement; and*

*establishing a communication link corresponding to a user selection of an icon displayed on the graphical user interface.*

*39. The method of claim 38, wherein the reduced number of icons displayed comprises only a single icon.*

*40. The method of claim 39, wherein the single icon comprises an icon for dialing an emergency number.*

*41. The method of claim 40, wherein the icon for dialing an emergency number occupies virtually the entire graphical user interface.*

*42. The method of claim 38, further comprising adjusting sizes of the reduced number of icons based on the number of icons displayed.*

*43. The method of claim 38, wherein the at least one biometric measurement includes at least one of heart rate, blood pressure, pulse, hand humidity, perspiration, blood oxygen level, temperature, blood sugar level, and shakiness of a hand of the user.*

*44. The method of claim 43, wherein the at least one biometric measurement is measured by the at least one additional sensor.*

*45. The method of claim 44, wherein one or more of the sensor for measuring acceleration and the at least one additional sensor is integrated into the mobile device.*

*46. The method of claim 44, wherein one or more of the sensor for measuring acceleration and the at least one additional sensor is separate from the mobile device.*

*47. The method of claim 46, wherein one or more of the sensor for measuring acceleration and the at least one additional sensor communicates with the mobile device over a short range communication interface.*

*48. The method of claim 38, further comprising determining a type of information that is displayed based on at least one of the measurement of acceleration and the at least one biometric measurement.*

*49. The method of claim 38, wherein the displayed information includes at least one icon.*

*50. The method of claim 38, wherein the displayed information includes phone numbers of emergency contacts for the user.*

*51. The method of claim 38, wherein establishing the communication link comprises one of the following:*

*launching an internet browser;*

*making a phone call;*

*launching a navigation application; or*

*sending a text message.*

*52. The method of claim 38, wherein reducing the number of icons displayed comprises calculating a metric based on at least one of the acceleration measurement and the at least one biometric measurement and comparing the metric to a threshold value.*

*53. The method of claim 38, wherein the sensor for measuring acceleration is an accelerometer.*

*54. The method of claim 38, wherein one or more of the measurement of acceleration and the at least one biometric measurement indicate a worsening user condition.*

*55. A non-transitory computer-readable medium storing a computer program comprising computer readable instructions, which when run on a mobile device causes the mobile device to:*

*display a plurality of icons on a graphical user interface of the mobile device;*

*obtain, from a sensor for measuring acceleration, a measurement of acceleration of a user of the mobile device;*

*obtain, from at least one additional sensor, at least one biometric measurement of the user of the mobile device;*

*reduce a number of the icons displayed on the graphical user interface based on the measurement of acceleration and the at least one biometric measurement; and*

*establish a communication link corresponding to a user selection of an icon displayed on the graphical user interface.*

*56. The non-transitory computer-readable medium of claim 55, wherein the reduced number of icons displayed comprises only a single icon.*

*57. The non-transitory computer-readable medium of claim 56, wherein the single icon comprises an icon for dialing an emergency number.*

*58. The non-transitory computer-readable medium of claim 57, wherein the icon for dialing an emergency number occupies virtually the entire graphical user interface.*

*59. The non-transitory computer-readable medium of claim 55, wherein the mobile device is further caused to adjust sizes of the reduced number of icons based on the number of icons displayed.*

*60. The non-transitory computer-readable medium of claim 55, wherein the at least one biometric measurement includes at least one of heart rate, blood pressure, pulse, hand humidity, perspiration, blood oxygen level, temperature, blood sugar level, and shakiness of a hand of the user.*

*61. The non-transitory computer-readable medium of claim 60, wherein the at least one biometric measurement is measured by the at least one additional sensor.*

*62. The non-transitory computer-readable medium of claim 61, wherein one or more of the sensor for measuring acceleration and the at least one additional sensor is integrated into the mobile device.*

*63. The non-transitory computer-readable medium of claim 61, wherein one or more of the sensor for measuring acceleration and the at least one additional sensor is separate from the mobile device.*

*64. The non-transitory computer-readable medium of claim 63, wherein one or more of the sensor for measuring acceleration and the at least one additional sensor communicates with the mobile device over a short range communication interface.*

*65. The non-transitory computer-readable medium of claim 55, wherein the mobile device is further caused to determine a type of information that is displayed based on at least one of the measurement of acceleration and the at least one biometric measurement.*

*66. The non-transitory computer-readable medium of claim 55, wherein the displayed information includes at least one icon.*

*67. The non-transitory computer-readable medium of claim 55, wherein the displayed information includes phone numbers of emergency contacts for the user.*

*68. The non-transitory computer-readable medium of claim 55, wherein establishing the communication link comprises one of the following:*

*launching an internet browser;*

*making a phone call;*

*launching a navigation application; or*

*sending a text message.*

*69. The non-transitory computer-readable medium of claim 55, wherein the number of icons displayed on the graphical user interface are reduced by calculating a metric based on at least one of the acceleration measurement and the at least one biometric measurement and comparing the metric to a threshold value.*

*70. The non-transitory computer-readable medium of claim 55, wherein the sensor for measuring acceleration is an accelerometer.*

*71. The non-transitory computer-readable medium of claim 55, wherein one or more of the measurement of acceleration and the at least one biometric measurements indicate a worsening user condition.*

*72. A mobile device comprising:*

*a transceiver;*

*a memory;*

*and*

*processing circuitry configured to:*

*play music;*

*display a plurality of icons on a graphical user interface of the mobile device;*

*obtain, from a sensor for measuring acceleration, a measurement of acceleration of a user of the mobile device;*

*obtain, from at least one additional sensor, at least one biometric measurement of the user of the mobile device;*

*reduce a number of the icons displayed on the graphical user interface based on the measurement of acceleration and the at least one biometric measurement indicating that the user is engaged in a physical activity.*

*73. The mobile device of claim 72, wherein the at least one biometric measurement includes measurements for at least one of elevated heart rate, shaking, vibration, blood pressure, pulse, hand humidity, perspiration, blood oxygen level, temperature, and blood sugar level.*

*74. The mobile device of claim 72, wherein the reduced number of icons displayed comprise play, skip, pause, and stop icons.*

*75. The mobile device of claim 72, wherein the processing circuitry is further configured to adjust sizes of the reduced number of icons based on the number of icons displayed.*

*76. The mobile device of claim 72, wherein the reduced number of icons displayed comprises icons that are more pertinent to the user in his or her current condition, as determined by the measurement of acceleration and the at least one biometric measurement.*

*77. The mobile device of claim 72, wherein the sensor for measuring acceleration is an accelerometer.*

* * * * *